United States Patent
Finley (10) Patent No.: US 9,421,051 B2
(45) Date of Patent: Aug. 23, 2016

(54) IMPLANT FIXATION ASSEMBLY

(71) Applicant: Biomet Manufacturing, LLC, Warsaw, IN (US)

(72) Inventor: Adam Finley, Leesburg, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 246 days.

(21) Appl. No.: 14/019,666

(22) Filed: Sep. 6, 2013

(65) Prior Publication Data

US 2015/0073489 A1    Mar. 12, 2015

(51) Int. Cl.
| | | |
|---|---|---|
| *A61B 17/84* | (2006.01) | |
| *A61B 17/88* | (2006.01) | |
| *A61B 17/68* | (2006.01) | |
| *A61F 2/30* | (2006.01) | |
| *A61F 2/36* | (2006.01) | |
| *A61F 2/40* | (2006.01) | |

(52) U.S. Cl.
CPC ............. *A61B 17/844* (2013.01); *A61B 17/683* (2013.01); *A61F 2/30749* (2013.01); *A61F 2/3601* (2013.01); *A61F 2/4081* (2013.01); *A61F 2002/30462* (2013.01); *A61F 2002/30507* (2013.01); *A61F 2002/30566* (2013.01)

(58) Field of Classification Search
CPC .... A61B 17/68; A61B 17/683; A61B 17/688; A61B 17/84; A61B 17/844; A61B 2017/681; A61F 2/36; A61F 2/3601; A61F 2/3603; A61F 2/4081; A61F 2002/30462; A61F 2002/30565; A61F 2002/30566; A61F 2002/4085

See application file for complete search history.

(56) References Cited

U.S. PATENT DOCUMENTS

| | | | | |
|---|---|---|---|---|
| 2,397,545 | A * | 4/1946 | Hardinge | A61B 17/746 411/54 |
| 3,051,169 | A * | 8/1962 | Grath | A61B 17/742 606/65 |
| 4,024,588 | A * | 5/1977 | Janssen | A61F 2/30 623/18.12 |
| 4,129,903 | A * | 12/1978 | Huggler | A61F 2/3601 606/67 |
| 4,621,629 | A * | 11/1986 | Koeneman | A61B 17/746 606/65 |
| 4,673,407 | A * | 6/1987 | Martin | A61F 2/38 623/20.33 |
| 4,947,502 | A * | 8/1990 | Engelhardt | A61B 17/86 411/392 |
| 4,959,064 | A * | 9/1990 | Engelhardt | A61B 17/86 411/544 |

(Continued)

FOREIGN PATENT DOCUMENTS

WO    2012/125704 A2    9/2012

*Primary Examiner* — Christian Sevilla
*Assistant Examiner* — Eric S Gibson
(74) *Attorney, Agent, or Firm* — Schwegman Lundberg & Woessner, P.A.

(57) ABSTRACT

An implant fixation assembly for securing an implant to a bone includes a first member, a stem, a biasing member and a tensioner. The first member includes a bone-engagement surface. The stem extends from the first member for insertion into a bore formed in the bone. The biasing member biases a distal portion of the stem toward the bone-engagement surface. The tensioner pre-tensions the biasing member.

18 Claims, 6 Drawing Sheets

(56) References Cited

U.S. PATENT DOCUMENTS

| | | | | |
|---|---|---|---|---|
| 5,007,935 A * | 4/1991 | Vincent | A61F 2/3061 | 623/23.14 |
| 5,800,553 A * | 9/1998 | Albrektsson | A61B 17/1668 | 606/65 |
| 5,800,557 A * | 9/1998 | Elhami | A61B 17/1753 | 623/23.12 |
| 5,827,285 A * | 10/1998 | Bramlet | A61B 17/68 | 411/166 |
| 6,197,065 B1 * | 3/2001 | Martin | A61B 17/164 | 623/23.17 |
| 6,508,841 B2 * | 1/2003 | Martin | A61B 17/164 | 623/23.12 |
| 6,656,184 B1 * | 12/2003 | White | A61B 17/8625 | 606/318 |
| 6,712,855 B2 * | 3/2004 | Martin | A61B 17/164 | 623/20.34 |
| 7,141,073 B2 * | 11/2006 | May | A61B 17/164 | 623/32 |
| 7,175,626 B2 * | 2/2007 | Neff | A61B 17/7225 | 606/86 A |
| 7,476,254 B2 * | 1/2009 | White | A61B 17/8066 | 623/22.32 |
| 7,503,919 B2 * | 3/2009 | Shaw | A61B 17/746 | 606/65 |
| 7,621,962 B2 * | 11/2009 | Lakin | A61F 2/32 | 623/22.15 |
| 7,662,173 B2 * | 2/2010 | Cragg | A61B 17/70 | 606/279 |
| 7,722,678 B2 * | 5/2010 | Brown | A61B 17/164 | 606/282 |
| 7,833,256 B2 * | 11/2010 | Biedermann | A61B 17/7004 | 606/300 |
| 7,905,908 B2 * | 3/2011 | Cragg | A61B 17/70 | 606/279 |
| 7,909,882 B2 * | 3/2011 | Stinnette | A61F 2/32 | 623/22.15 |
| 8,182,484 B2 * | 5/2012 | Grant | A61B 17/746 | 606/62 |
| 8,292,967 B2 * | 10/2012 | Brown | A61B 17/0401 | 623/23.19 |
| 8,449,574 B2 * | 5/2013 | Biedermann | A61B 17/7004 | 606/246 |
| 8,512,416 B2 * | 8/2013 | Porter | A61F 2/78 | 623/16.11 |
| 8,579,985 B2 * | 11/2013 | Podolsky | A61F 2/4609 | 623/22.42 |
| 8,702,768 B2 * | 4/2014 | Tipirneni | A61B 17/68 | 606/320 |
| 8,828,067 B2 * | 9/2014 | Tipirneni | A61B 17/742 | 606/320 |
| 8,915,970 B2 * | 12/2014 | Porter | A61F 2/2814 | 623/16.11 |
| 8,968,415 B2 * | 3/2015 | Meridew | A61F 2/30749 | 623/22.4 |
| 9,023,115 B2 * | 5/2015 | Porter | A61F 2/78 | 623/16.11 |
| 9,028,534 B2 * | 5/2015 | Tipirneni | A61B 17/742 | 606/320 |
| 2001/0051831 A1 * | 12/2001 | Subba Rao | A61F 2/3609 | 623/22.42 |
| 2002/0107520 A1 * | 8/2002 | Hoffman | A61B 17/15 | 623/23.11 |
| 2003/0032958 A1 * | 2/2003 | Soubeiran | A61B 17/7216 | 606/250 |
| 2003/0149485 A1 * | 8/2003 | Tornier | A61F 2/30721 | 623/18.11 |
| 2004/0172138 A1 * | 9/2004 | May | A61B 17/164 | 623/20.36 |
| 2004/0220673 A1 * | 11/2004 | Pria | A61F 2/4081 | 623/19.12 |
| 2005/0113919 A1 * | 5/2005 | Cragg | A61B 17/70 | 623/17.11 |
| 2006/0129247 A1 * | 6/2006 | Brown | A61B 17/164 | 623/23.46 |
| 2006/0241779 A1 * | 10/2006 | Lakin | A61F 2/32 | 623/22.15 |
| 2007/0067038 A1 * | 3/2007 | Studer | A61F 2/4425 | 623/17.13 |
| 2007/0100458 A1 * | 5/2007 | Dalla Pria | A61F 2/30721 | 623/19.13 |
| 2007/0233255 A1 * | 10/2007 | Song | A61F 2/4425 | 623/17.11 |
| 2008/0195145 A1 * | 8/2008 | Bonutti | A61B 17/0401 | 606/207 |
| 2011/0034959 A1 * | 2/2011 | Sevrain | A61B 17/688 | 606/324 |
| 2011/0137356 A1 * | 6/2011 | Kollmer | A61B 17/1767 | 606/324 |
| 2011/0190907 A1 * | 8/2011 | Porter | A61F 2/78 | 623/32 |
| 2012/0053630 A1 * | 3/2012 | Denham | A61B 17/0401 | 606/232 |
| 2012/0101456 A1 * | 4/2012 | Forsell | A61F 2/30721 | 604/264 |
| 2013/0041414 A1 * | 2/2013 | Epperly | A61B 17/7225 | 606/310 |
| 2013/0204387 A1 * | 8/2013 | Meridew | A61F 2/30749 | 623/22.32 |
| 2013/0331896 A1 * | 12/2013 | Holt | A61B 17/0487 | 606/328 |
| 2014/0155944 A1 * | 6/2014 | Truman | A61B 17/0401 | 606/324 |
| 2014/0194907 A1 * | 7/2014 | Bonutti | A61B 17/8866 | 606/151 |
| 2014/0257294 A1 * | 9/2014 | Gedet | A61B 17/842 | 606/80 |
| 2014/0277175 A1 * | 9/2014 | Campbell | A61B 17/809 | 606/281 |
| 2015/0025641 A1 * | 1/2015 | Masson | A61F 2/4014 | 623/19.13 |
| 2015/0073489 A1 * | 3/2015 | Finley | A61B 17/844 | 606/320 |

* cited by examiner

IMPLANT FIXATION ASSEMBLY

FIELD

The present disclosure relates to an implant fixation assembly, and more particularly to a device and method for securing a glenoid component to a glenoid through continuous loading.

BACKGROUND

This section provides background information related to the present disclosure which is not necessarily prior art.

A surgical implant may be securely fastened to a bone in a variety of ways, including mechanical fasteners, adhesive, and frictionally-engaged pegs. When a bone implant is securely fastened to a bone, the bone may grow around the implant, further strengthening the interface between the bone and the bone implant. Over time, and as a result of compressive and frictional forces between the bone and the bone implant, the bone may begin to recede at the interface. As the bone begins to recede, the bone implant may loosen with respect to the bone, such that there is movement in the interface between the bone and the bone implant. Movement between the bone and the bone implant may prevent the bone from growing around the bone implant. In addition, it may be difficult to re-secure the bone implant to the bone, since the quality of the bone (e.g., thickness, density, size, etc.) may be such that additional attachment efforts will further deteriorate the bone and/or lead to medical complications.

SUMMARY

This section provides a general summary of the disclosure, and is not a comprehensive disclosure of its full scope or all of its features.

According to one particular aspect, the present disclosure provides an implant fixation assembly for securing an implant to a bone. The implant fixation assembly includes a first member, a stem, a biasing member and a tensioner. The first member includes a bone-engagement surface. The stem extends from the first member for insertion into a bore formed in the bone. The biasing member biases a distal portion of the stem toward the bone-engagement surface. The tensioner pre-tensions the biasing member.

According to another particular aspect, the present disclosure provides an implant fixation assembly for securing an implant to a bone. The implant fixation assembly includes a bone-engaging member, a stem, a biasing member, a tensioner, a spacer and an anchoring mechanism. The bone-engaging member engages an external bone surface. The stem has a longitudinal axis and a distal end. The stem is adapted to be inserted into a bore formed in the bone such that the distal end engages an interior surface of the bore to oppose further movement of the stem along the longitudinal axis. The biasing member biases the distal portion of the stem toward the bone-engaging member. The tensioner pre-tensions the biasing member prior to implantation of the assembly. The spacer has a flanged distal end opposing the distal end of the stem. The spacer extends through the tensioner and is slidable relative to the tensioner. The anchoring mechanism anchors the distal end of the stem relative to the bone.

According to yet another particular aspect, the present disclosure provides a method of securing an implant fixation assembly to a bone. The method includes providing an implant fixation assembly. The implant fixation assembly includes an adaptor portion, a stem portion, and a biasing member. The biasing member biases a distal end of the stem portion toward the adaptor portion. The method also includes pre-tensioning the biasing member prior to implantation of the assembly. The method additionally includes inserting the stem into a bore of the bone. The method further includes releasing a pre-tension of the biasing member such that the biasing member draws the adaptor against an external surface of the bone.

According to another particular aspect, the present disclosure provides an implant fixation assembly for securing an implant to a bone. The implant fixation assembly includes a first member, a plate, and a biasing member. The first member has a proximal surface and a distal surface. The distal surface of the first member includes at least one fin projecting therefrom for insertion into a recess formed in the bone. The proximal surface of the first member includes a recess extending in a first direction. The plate is at least partially disposed within the recess and is operable to traverse at least a portion of the recess in the first direction. The biasing member is disposed between the plate and the first member and is operable to bias the bone-engagement surface toward the bone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-7, an implant fixation assembly constructed in accordance with the present teachings is illustrated and identified at reference character 10. The implant fixation assembly 10 may be used to secure an implant (not shown) to a bone 12. According to one exemplary use, the implant fixation assembly 10 may be used to fix a glenoid implant (not shown) to a glenoid. It will also be appreciated, however, that the present teachings may be adapted to fix various implants to various bones. By way of example only, the implant fixation assembly 10 may be used to fix a humeral head implant to a humeral shaft or to fix a femoral head implant to a femoral shaft.

The implant fixation assembly 10 may generally include a first member, a tensioner 16, a spacer 18, and a support or anchoring mechanism 20. As illustrated, the first member may be an adaptor 14 to which an implant may be secured. Alternatively, the first member may integrally or otherwise include the implant.

Figure 1:
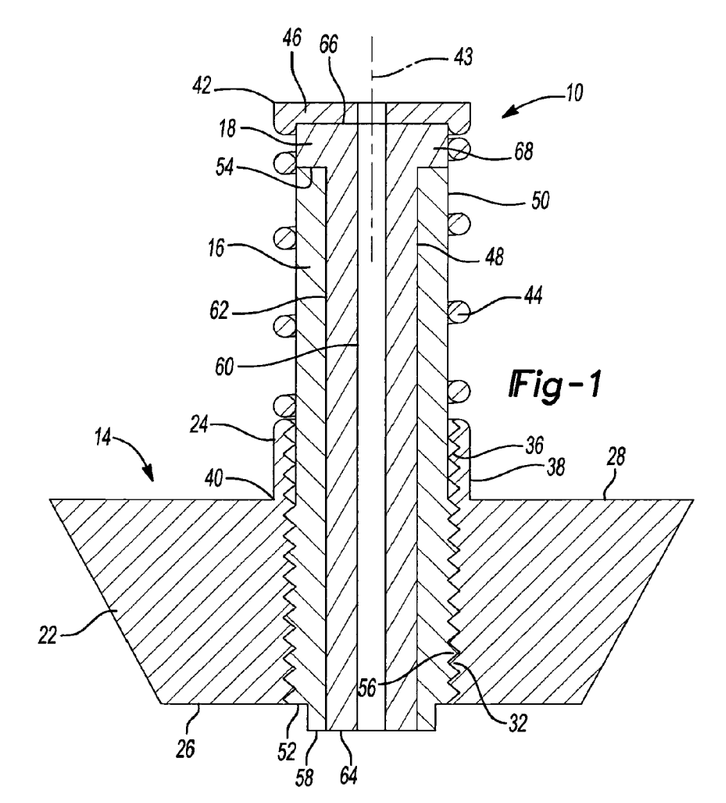
FIG. 1 is a cross-sectional view of an implant fixation assembly in a first configuration, in accordance with the teachings of the present disclosure.
Figure 2:
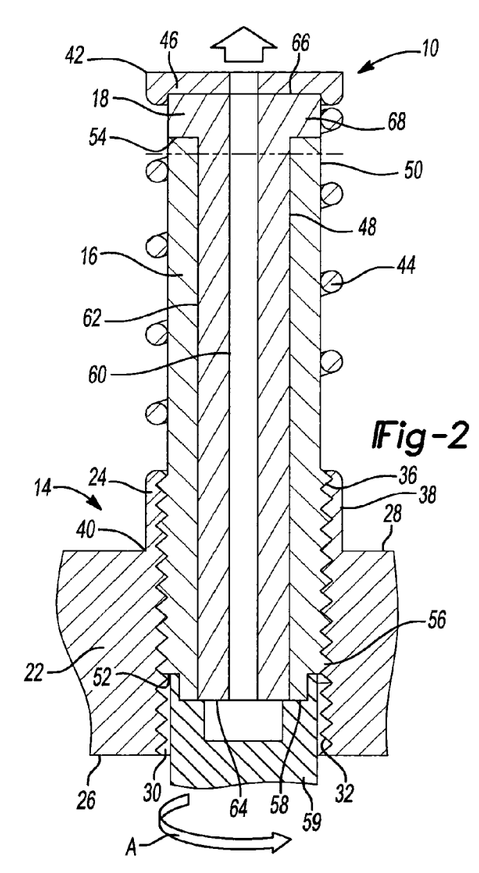
FIG. 2 is a cross-sectional view of the implant fixation assembly of FIG. 1 in a second configuration.

The adaptor 14 may include a bone-engaging portion 22 and a projection or stem portion 24. The bone-engaging portion 22 may include a proximal end surface 26, a distal end surface 28, and a bore or aperture 30 extending between the proximal end surface 26 and the bone-engagement, or distal end surface 28. As illustrated, the proximal end surface 26 and the distal end surface 28 may be generally planar and oriented generally parallel to one another. The bone-engaging portion 22 may be formed from a polymer, a ceramic, a metal, or other suitable biocompatible material.

The proximal end surface 26 may engage an implant (not shown), such as a glenoid liner, a glenosphere head, or a glenoid tray. It will be understood that such engagement is conventional in the art insofar as the present teachings are concerned. The distal end surface 28 may engage a bone 12.

As illustrated, the proximal end surface 26 and the distal end surface 28 may be generally circular. The proximal end surface 26 may be smaller than the distal end surface 28 such that the bone-engaging portion 22 has a tapered profile extending between the proximal end surface and the distal end surface. As such, the adaptor 14 may generally have the shape of a truncated cone. The tapered profile of the adaptor 14 may receive, or mate to, a corresponding tapered portion of the implant.

The aperture 30 may include a threaded portion 32 at least adjacent to the distal end surface 28. The threaded portion 32 may receive the tensioner 16.

The stem portion 24 of the adaptor 14 may be monolithically formed with the bone-engaging portion 22. In the embodiment illustrated, the stem portion 24 may be wired in a helix to create a spring while keeping the stem portion 24 in one piece. The stem portion 24 may generally define a hollow cylinder extending from a proximal end 40 to a distal end 42 thereof, along a longitudinal axis 43.

A biasing member or helical spring element 44 may extend between the proximal end 40 and the distal end 42 of the stem portion 24 and be integrally formed therewith by machining or through other suitable manufacturing process. Alternatively, a discrete spring member may be incorporated within the scope of the present teachings. The helical spring element 44 may allow the distal end surface 28 of the adaptor 14 and a proximal end 40 of the stem portion 24 to be biased relative to the distal end 42 of the stem portion 24.

In one configuration, the proximal end 40 of the stem portion 24 may be integrally formed with the distal end surface 28 of the bone-engaging portion 22. In this regard, the stem portion 24 may be an extruded portion of the bone-engaging portion 22. It is also understood that the stem portion 24 may be separately formed from, and fastened to, the distal end surface 28 of the bone-engaging portion 22 with mechanical fasteners, adhesive, welding, or similar fastening techniques. The distal end 42 of the stem portion 24 may include a lipped or flanged portion 46 integrally formed therewith.

The tensioner 16 may pre-tension the biasing member prior to implantation or during surgery, and may include an inner wall 48 and an outer wall 50 and may generally define a hollow cylinder extending from a proximal end 52 to a distal end 54. The tensioner 16 may be formed from a polymer, a ceramic, a metal, or other suitable biocompatible material. A diameter of the outer wall 50 of the tensioner 16 may be such that the outer wall 50 may slide within and relative to the inner wall 36 of the stem portion 24. The outer wall 50 may include a threaded portion 56 adjacent to the proximal end 52. The threaded portion 56 may receive and threadingly engage the threaded portion 32 of the bone-engaging portion 22.

The proximal end 52 of the tensioner 16 may include a head portion 58 integrally formed therewith. The head portion 58 may be a hex head or other configuration that can be suitably secured by a wrench 59 (see FIG. 2) or similar driver to rotate the tensioner 16 and secure the threaded portion 56 with the threaded portion 32 of the bone-engaging portion 22. Rotation of the wrench 59 to turn the tensioner 16 relative to the adaptor 14 and correspondingly advance the tensioner 16 in a linear direction is shown at arrow A. Accordingly, in a first position (FIG. 2), the tensioner 16 may apply a pre-tension force in the biasing member 44, and in a second position (FIG. 1) the tensioner 16 may release the pre-tension force from the biasing member 44.

The spacer 18 may be concentrically disposed within the tensioner 16 such that the tensioner 16 is concentrically between the tensioner 16 and the stem portion 24 of the adaptor 14. The spacer 18 may include an inner wall 60 and an outer wall 62 and may generally define a hollow cylinder extending from a proximal end 64 to a distal end 66. The tensioner 16 may be formed from a polymer, a ceramic, a metal, or other suitable biocompatible material. The diameter of the outer wall 62 may be such that the outer wall 62 slides within the inner wall 48 of the tensioner 16. The distal end 66 of the spacer 18 may include a lipped or flanged portion 68 integrally formed therewith.

The anchoring mechanism 20 may operate to anchor the distal end of the stem relative to the bone. The anchoring mechanism may be a flexible member construct 20. In the embodiment illustrated, the flexible member construct 20 may include a flexible member 70 and an anchor 72. One suitable flexible member construct-type is disclosed in commonly assigned U.S. Pat. Pub. No. 2012/0053630. The disclosure of U.S. Pat. Pub. No. 2012/0053630 is hereby incorporated by reference as if fully set forth herein.

Operation of the implant fixation assembly 10 will now be described in more detail. With reference to FIG. 1, the spacer 18 may be placed within the adaptor 14 such that the flanged portion 68 of the spacer 18 rests against the flanged portion 46 of the stem portion 24. The tensioner 16 may be placed within the adaptor 14 such that the distal end 54 of the tensioner 16 rests against the flanged portion 68 of the spacer 18.

The tensioner 16 may be rotated in a first direction such that the threaded portion 56 of the tensioner 16 engages the threaded portion 32 of the bone-engaging portion 22, thus increasing the distance between the proximal end 52 of the tensioner 16 and the proximal end surface 26 of the bone-engaging portion 22. Upon threading the threaded portion 56 of the tensioner 16 into the threaded portion 32 of the bone-engaging portion 22, the distal end 54 of the tensioner 16 may apply a force on the distal end 66 of the spacer 18 such that the helical spring element 44 is extended (i.e., pre-tensioned) and the distal end 42 of the stem portion 24 is biased away from the proximal end 40 of the stem portion (FIG. 1). The biasing force of the helical spring element 44 may be transmitted through the tensioner 16.

Figure 3:
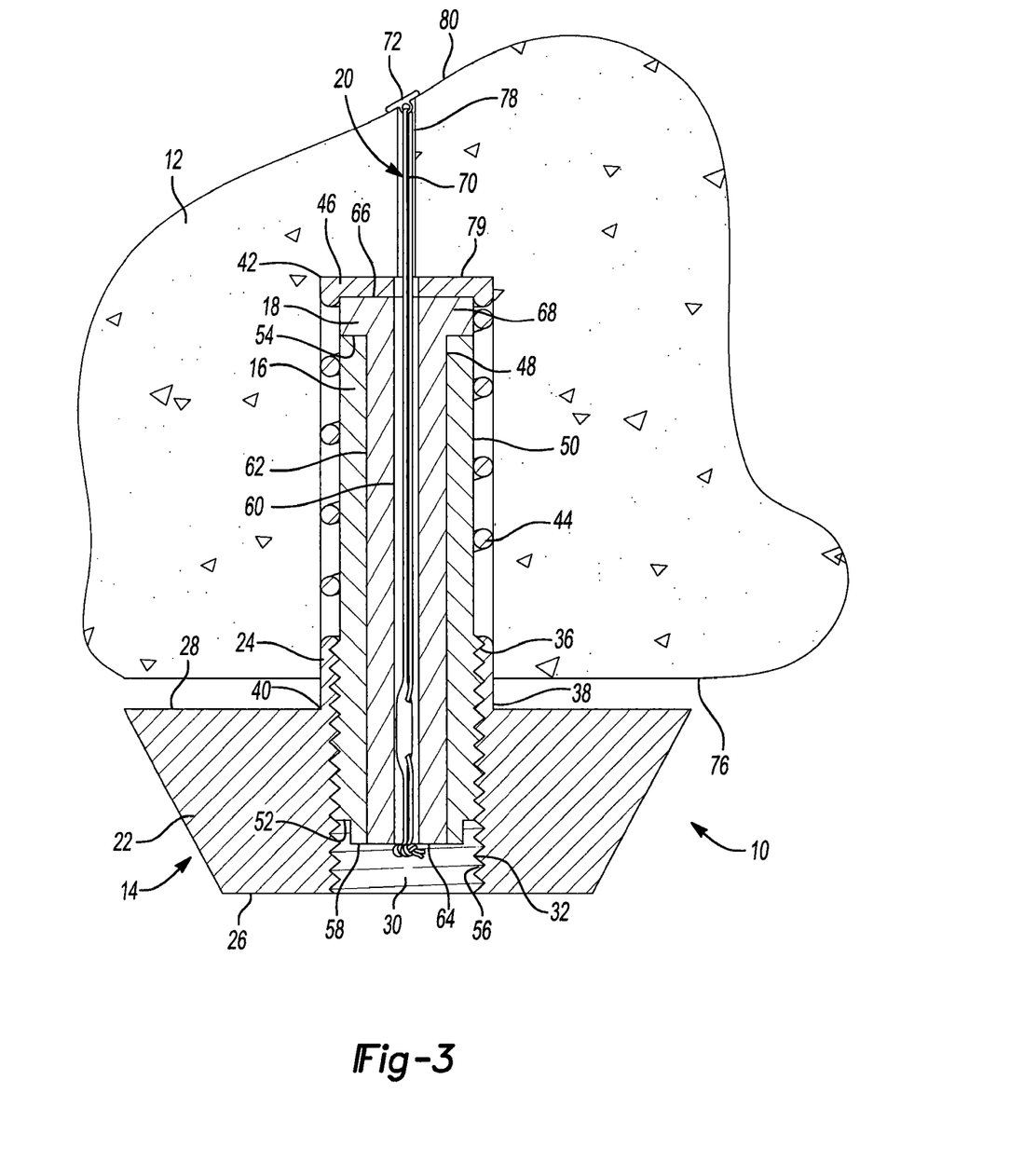
FIG. 3 is an environmental view illustrating the implant fixation assembly of the present teachings in the first configuration, the implant fixation assembly shown operatively implanted within a bone.
Figure 4:
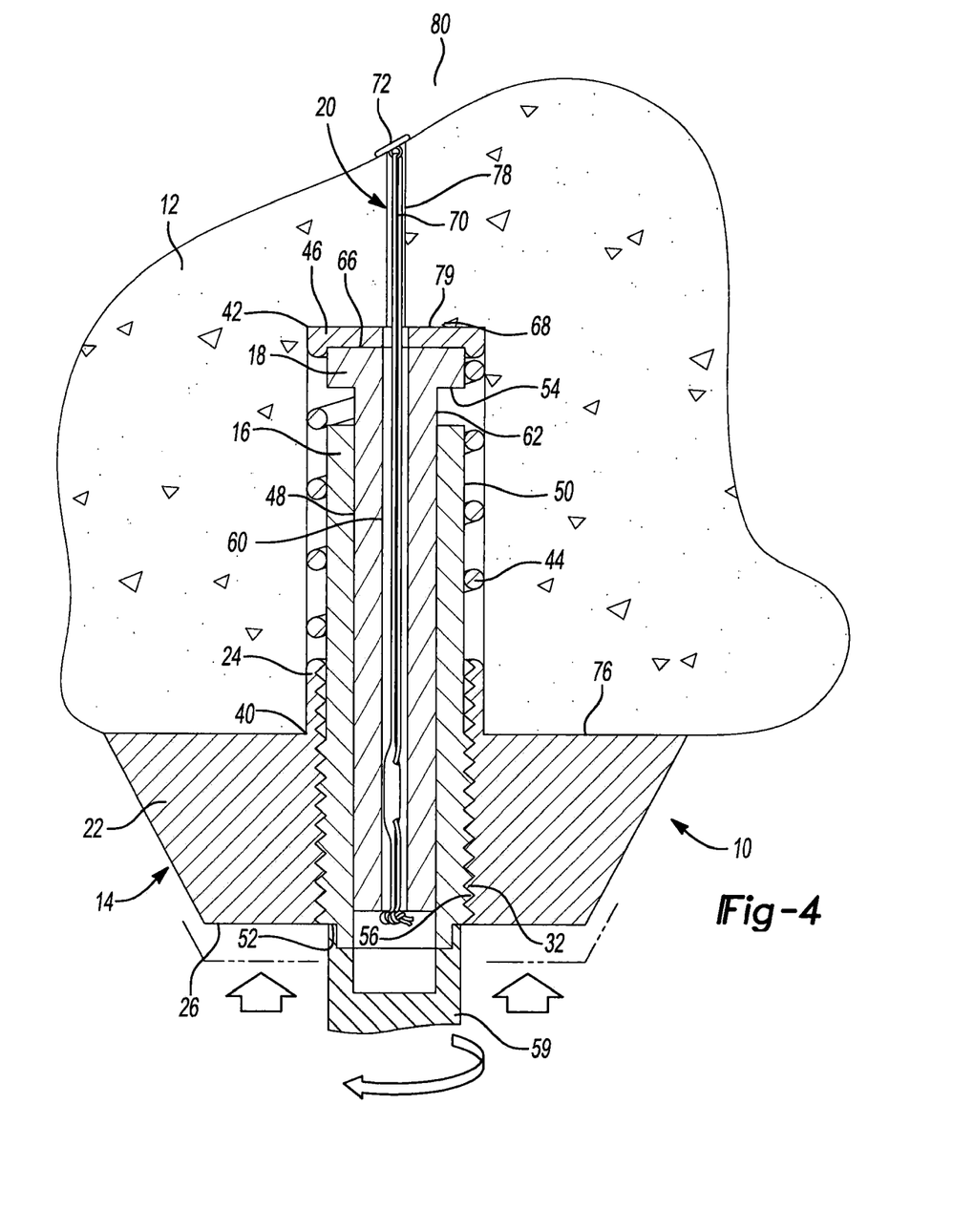
FIG. 4 is an environmental view similar to FIG. 3, the implant fixation assembly shown in the second configuration.
Figure 5:
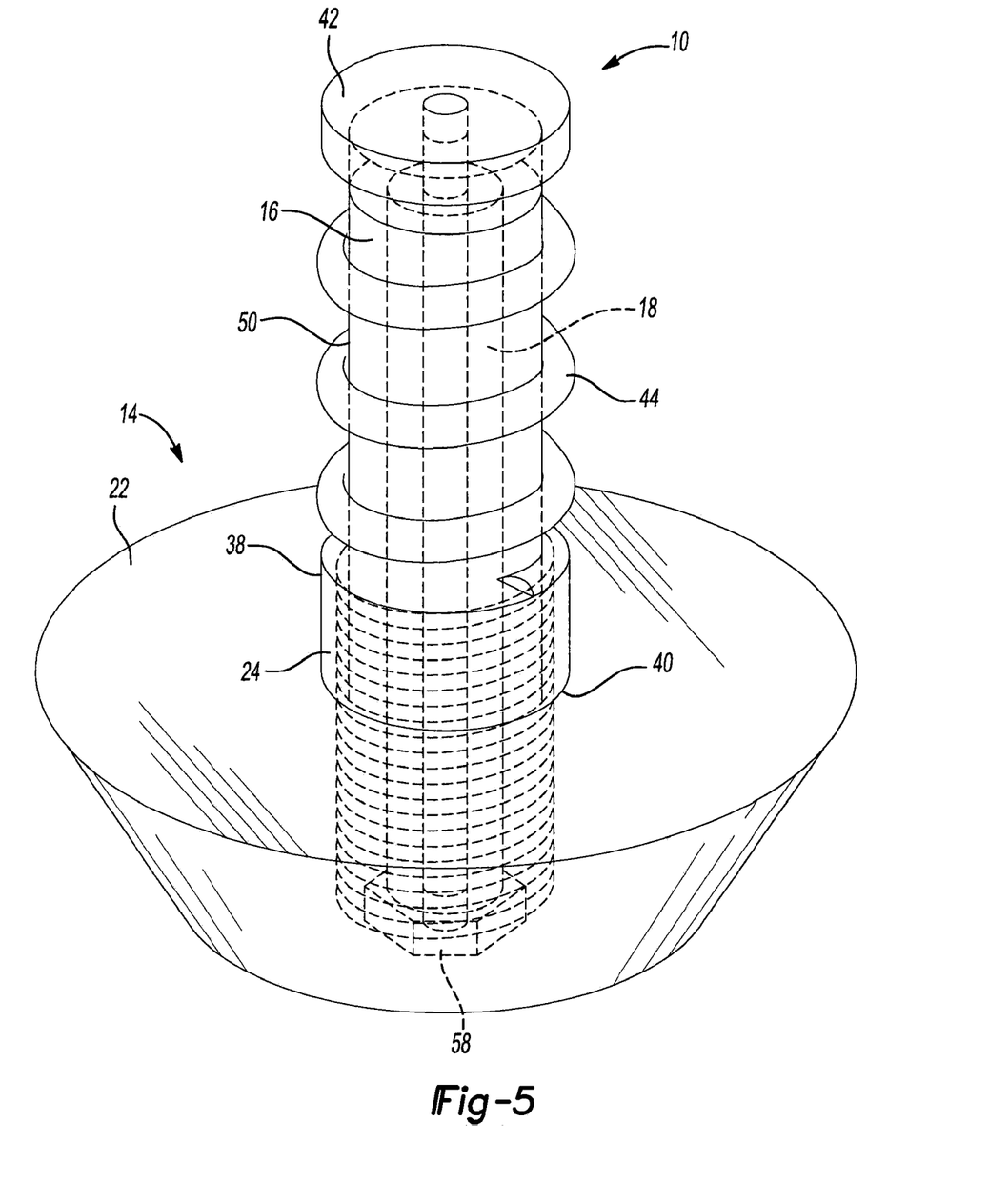
FIG. 5 is a perspective view of the implant fixation assembly of the present teachings.
Figure 6:
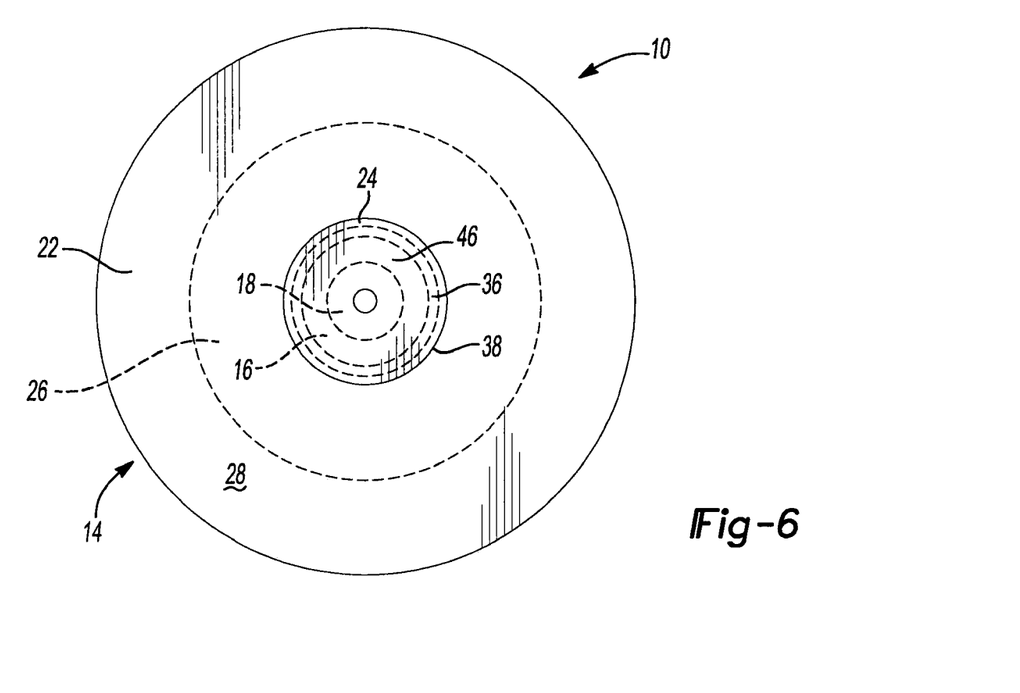
FIG. 6 is a top view of the implant fixation assembly of the present teachings.
Figure 7:
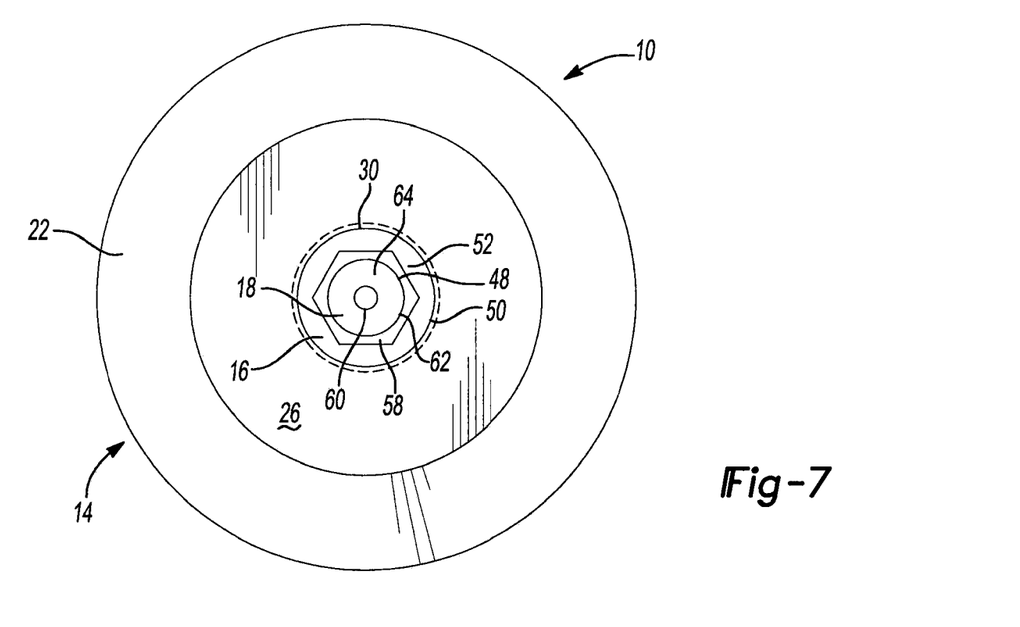
FIG. 7 is a bottom view of the implant fixation assembly of the present teachings.

With particular reference to FIGS. 3 and 4, the bone 12 may be prepped for the implant fixation assembly 10 by forming a recess or bore 74 in a first surface 76 of the bone 12 and forming an aperture 78 that extends from an end 79 of the bore 74 to a second surface 80 of the bone. The adaptor 14, the tensioner 16 and the spacer 18 may be placed in the bore 74 of the bone 12. The flexible member construct 20 may be placed within the aperture 78 of the bone 12 and extended through the spacer 18 from the proximal end 64 to the distal end 66 thereof. The anchor 72 of the flexible member construct 20 may be secured against the second surface 80 of the bone 12 by tightening the flexible member 70 against the proximal end 64 of the spacer 18. Securing the anchor 72 against the bone 12 will secure the implant fixation assembly 10, and specifically the distal end 42 of the stem portion 24, to the end 79 of the bore 74.

Upon securing the flexible member construct 20 within the bore 74, as herein described, the tensioner 16 may be rotated in a second direction such that the threaded portion 56 of the tensioner 16 engages the threaded portion 32 of the bone-engaging portion 22. As the tensioner 16 is rotated in the second direction, the distance between the proximal end 52 of the tensioner 16 and the proximal end surface 26 of the bone-engaging portion 22 may decrease, and the distal end 54 of the tensioner 16 may no longer contact the distal end 66 of the spacer 18 (FIG. 4). Thus, the biasing or pre-tension force of the helical spring element 44 may be transferred from the tensioner 16 to the stem portion 24 of the adaptor 14, such that the distal end surface 28 of the bone-engaging portion 22 is biased into engagement with the first surface 76 of the bone 12. The flexible member construct 20 may establish a fixed distance between the bone 12 and the distal end 42 of the stem portion 24 such that the helical spring element 44, or other biasing member, biases the distal end surface 28 of the bone-engaging portion 22 against the bone 12 after the biasing or pre-tension force through the tensioner 16 is released.

As the bone 12 moves and adjusts over time, the first surface 76 of the bone 12 may wear or otherwise erode. In such a case, the biasing force of the helical spring element 44 will pull or bias the bone-engaging portion 22 closer to the distal end 54 of the tensioner 16 such that the distal end surface 28 of the bone-engaging portion 22 is continuously biased into engagement with the first surface 76 of the bone 12, despite such erosion of the bone 12.

Figure 8:
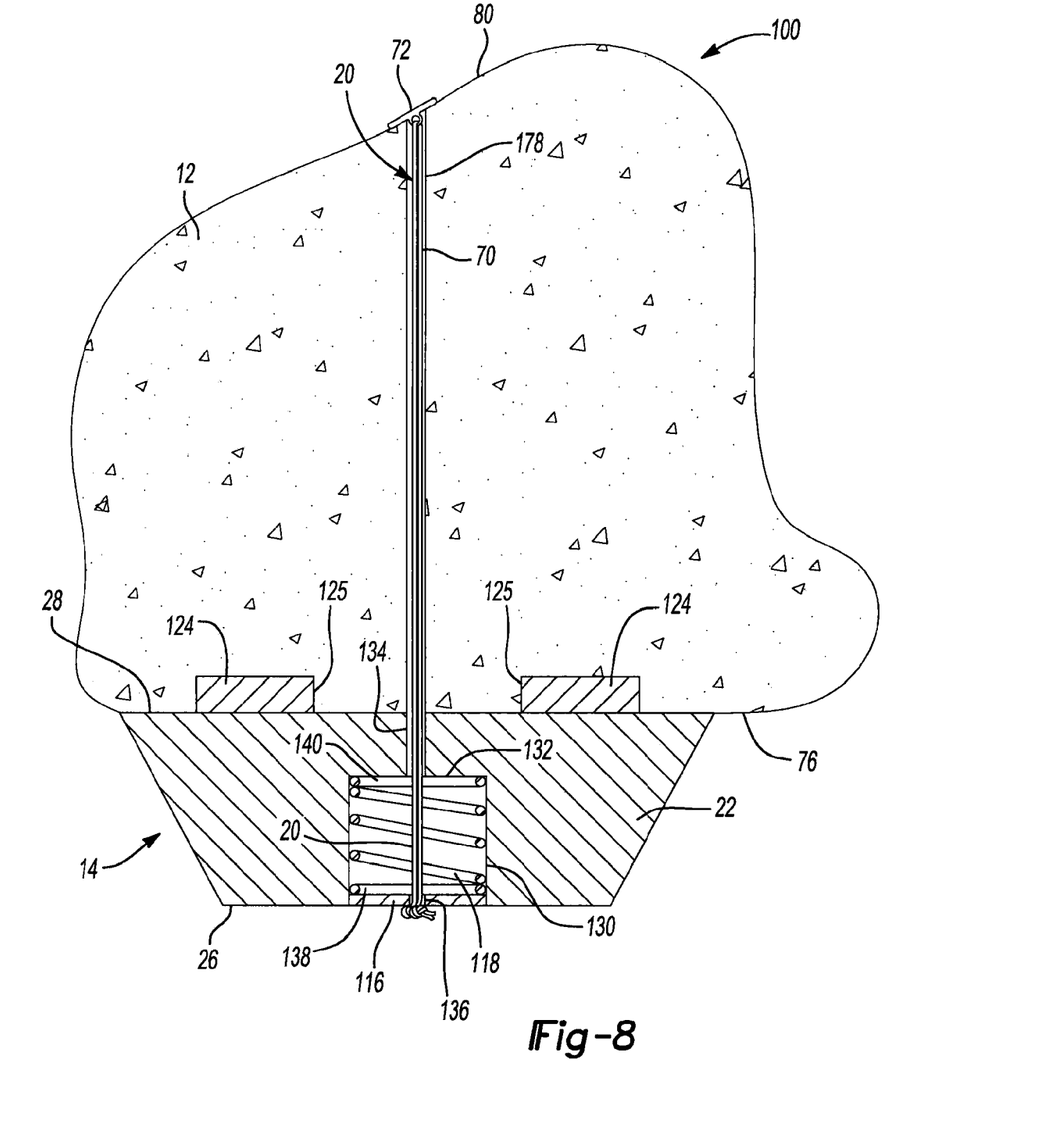
FIG. 8 is an environmental view illustrating an alternative embodiment of an implant fixation assembly in accordance with the present teachings, the implant fixation assembly shown operatively implanted within a bone.

Turning to FIG. 8, another implant fixation assembly in accordance with the present teachings is shown and identified at reference character 100. In view of the similarities between the implant fixation assembly 10 and the implant fixation assembly 100, like reference characters have been used to identify similar elements. The implant fixation assembly 100 primarily differs from the implant fixation assembly 10 in that the implant fixation assembly 100 does not include a stem.

The implant fixation assembly 100 may generally include a first member, a plate 116, a biasing member or helical spring element 118, and a support or anchoring mechanism 20. As illustrated, the first member may be an adaptor 14 to which an implant may be secured. Alternatively, the first member may integrally or otherwise include the implant.

The adaptor 14 may include at least one projection or fin 124 extending from the distal end surface 28 of the bone-engaging portion 22. The fin 124 may be a continuous, annular fin or any other suitably-shaped projection. Additionally, the fin 124 may be monolithically formed with the adaptor 14, or fixed to the adapter 14 with an adhesive, mechanical fastener, or other suitable securing technique. In an assembled configuration, at least a portion of the fin 124 may be positioned within a similarly-shaped recess 125 formed in the bone 12. Positioning the fin 124 within the similarly-shaped recess 125 will further secure the adaptor 14 to the bone 12, and specifically prevent the distal end surface 28 from sliding along, and rotating relative to, the bone 12. The proximal end surface 26 of the bone-engaging portion 22 may include a cavity or counter bore 130 defining an end 132. The distal end surface 28 of the bone-engaging portion 22 may include an aperture 134. The aperture 134 may extend between the end 132 of the counter bore 130 and the distal end surface 28 of the bone-engaging portion 22.

The plate 116 may be positioned within the similarly-shaped counter bore 130 and may be a washer-like element defining an aperture 136 therethrough. The perimeter of the plate 116 may be smaller than the perimeter of the counter bore 130, such that the plate 116 can traverse the length of the counter bore 130. The center of the aperture 136 may be substantially aligned with the center of the counter bore 130 and the center of the aperture 134, such that the apertures 134, 136 and the counter bore 130 define a substantially concentric passage between the proximal end surface 26 and distal end surface 28 of the bone-engaging portion 22.

The helical spring element 118 may be positioned within the counter bore 130, such that a proximal end 138 of the spring element 118 engages the plate 116 and a distal end 140 of the spring element 118 engages the end 132 of the counter bore 130. The helical spring element 118 may allow the plate 116 to be biased relative to the end 132 of the counter bore 130.

The anchoring mechanism 20 may extend through the aperture 136 of the plate, the counter bore 130 and the aperture 134 in the adaptor 14, and an aperture 178 in the bone 12. As will be described in more detail below, the anchoring mechanism 20 may operate to anchor the plate 116 relative to the bone 12.

Operation of the implant fixation assembly 100 will now be described in more detail. The bone 12 may be prepped for the implant fixation assembly 10 by forming a recess 125 in the first surface 76 of the bone 12 and forming the aperture 178 that extends from the first surface 76 of the bone 12 to the second surface 80 of the bone. The fin 124 may be placed within the recess 125, and the anchoring mechanism 20 may be extended through the aperture 178 of the bone 12, through the aperture 134 and the counter bore 130 in the adaptor 14 (including through the center of the helical spring 118), and through the aperture 136 of the plate 116. The anchor 72 of the flexible member construct 20 may be secured against the second surface 80 of the bone 12 by tightening the flexible member 70 against the plate 116. Tightening the flexible member 70 against the plate 116 will cause the plate 116 to move within the counter bore 130 and compress the helical spring 118 between the plate 116 and the end 132 of the counter bore 130, and establish a fixed distance between the plate 116 and the anchor 72. The compressive force of the spring 118 against the end 132 of the counter bore 130 will bias the distal end surface 28 of the adaptor 14 against the first surface 76 of the bone 12.

As the bone 12 moves and adjusts over time, the first surface 76 of the bone 12 may wear or otherwise erode. In such a case, the biasing force of the helical spring element 118 will push or bias the bone-engaging portion 22 closer to the first surface 76 of the bone 12 such that the distal end surface 28 of the bone-engaging portion 22 is continuously biased into engagement with the first surface 76 of the bone 12, despite such erosion of the bone 12.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An implant fixation assembly for securing an implant to a bone, the implant fixation assembly comprising:
    a first member having a bone-engagement surface;
    a stem extending from the first member for insertion into a bore formed in the bone;
    a helical spring configured to bias a distal portion of the stem toward the bone engagement surface;
    a rotatable member configured to pre-tension the helical spring; and
    an elongated flexible member construct configured to pass longitudinally through the stem and the bore of the bone to thereby anchor a distal end of the stem relative to the bone.

2. The implant fixation assembly of claim 1, wherein the helical spring is integrally formed with the stem.

3. The implant fixation assembly of claim 1, wherein the rotatable member is operative in a first position to pre-tension the helical spring and operative in a second position to release pre-tensioning from the helical spring.

4. The implant fixation assembly of claim 3, wherein the rotatable member linearly advances relative to the first member.

5. The implant fixation assembly of claim 3, wherein the rotatable member is threadably engaged with the first member.

6. The implant fixation assembly of claim 1, wherein the flexible member construct is operative to establish a fixed distance between the bone and the distal end of the stem such that the helical spring biases the bone engagement surface against the bone after the pre-tension of the rotatable member is released.

7. The implant fixation assembly of claim 6, wherein the flexible member construct includes a flexible member and an anchor.

8. The implant fixation assembly of claim 1, further comprising a spacer concentrically surrounded by the rotatable member and slidable relative to the rotatable member, the spacer having a distal end for engaging a distal end of the stem.

9. The implant fixation assembly of claim 1, wherein the rotatable member includes a hex portion that is securable by a wrench.

10. An implant fixation assembly for securing an implant to a bone, the implant fixation assembly comprising:
    a bone-engaging member for engaging an external bone surface;
    a stem having a longitudinal axis and a distal end, the stem adapted to be inserted into a bore formed in the bone such that the distal end engages an interior surface of the bore to oppose further movement of the stem along the longitudinal axis;
    a helical spring configured to bias a distal portion of the stem toward the bone-engaging member;
    a rotatable member configured to pre-tension the helical spring prior to implantation of the assembly;

a spacer extending through the rotatable member, the spacer slidable relative to the rotatable member and having a flanged distal end opposing the distal end of the stem; and an elongated flexible member construct configured to pass longitudinally through the stem and the bore of the bone to thereby anchor the distal end of the stem relative to the bone.

11. The implant fixation assembly of claim 10, wherein the rotatable member is operative in a first position to pre-tension the helical spring and operative in a second position to release pre-tensioning from the helical spring.

12. The implant fixation assembly of claim 11, wherein the rotatable member linearly advances relative to the bone-engaging member.

13. The implant fixation assembly of claim 11, wherein the rotatable member is threadably engaged with the bone-engaging member.

14. The implant fixation assembly of claim 10, wherein the flexible member construct is operative to establish a fixed distance between the bone and the distal end of the stem such that the helical spring biases the bone-engaging surface against the bone after the pre-tension of the rotatable member is released.

15. The implant fixation assembly of claim 10, wherein the flexible member construct includes a flexible member and an anchor.

16. The implant fixation assembly of claim 10, wherein the rotatable member includes a hex portion that is securable by a wrench.

17. An implant fixation assembly for securing an implant to a bone, the implant fixation assembly comprising:
a first member having a bone-engagement surface;
a stem extending from the first member for insertion into a bore formed in the bone;
a helical spring integrally formed with the stem and configured to bias a distal portion of the stem toward the bone engagement surface;
a rotatable member operative in a first position to pre-tension the helical spring and operative in a second position to release pre-tensioning from the helical spring, wherein the rotatable member is threadably engaged with the first member and configured to linearly advance relative to the first member;
an elongated flexible member construct configured to pass longitudinally through the stem and the bore of the bone to thereby anchor a distal end of the stem relative to the bone and operative to establish a fixed distance between the bone and the distal end of the stem such that the helical spring biases the bone engagement surface against the bone after the pre-tension of the rotatable member is released; and
a spacer concentrically surrounded by the rotatable member and slidable relative to the rotatable member, the spacer having a distal end for engaging the distal end of the stem.

18. An implant fixation assembly for securing an implant to a bone, the implant fixation assembly comprising:
a bone-engaging member for engaging an external bone surface;
a stem having a longitudinal axis and a distal end, the stem adapted to be inserted into a bore formed in the bone such that the distal end engages an interior surface of the bore to oppose further movement of the stem along the longitudinal axis;
a helical spring configured to bias a distal portion of the stem toward the bone-engaging member and engage an external bone surface;
a rotatable member for pre-tensioning the helical spring prior to implantation of the assembly, the rotatable member being operative in a first position to pre-tension the helical spring and operative in a second position to release pre-tensioning from the helical spring, the rotatable member being threadably engaged with the bone-engaging member and configured to advance linearly relative to the bone-engaging member,
a spacer extending through the rotatable member, the spacer slidable relative to the rotatable member and having a flanged distal end opposing the distal end of the stem; and
an elongated flexible member construct configured to pass longitudinally through the stem and the bore of the bone to thereby anchor the distal end of the stem relative to the bone,
the flexible member construct being operative to establish a fixed distance between the bone and the distal end of the stem such that the helical spring biases the bone-engaging surface against the bone after pre-tension of the rotatable member is released.

* * * * *